(12) United States Patent
Taylor

(10) Patent No.: US 9,822,337 B2
(45) Date of Patent: Nov. 21, 2017

(54) DEVICE FOR PERFORMING MICRO-OPERATIONS ON A VESICULAR OBJECT

(71) Applicant: Paul J. Taylor, Bozeman, MT (US)

(72) Inventor: Paul J. Taylor, Bozeman, MT (US)

( * ) Notice: Subject to any disclaimer, the term of this patent is extended or adjusted under 35 U.S.C. 154(b) by 0 days.

(21) Appl. No.: 13/986,508

(22) Filed: May 8, 2013

(65) Prior Publication Data
US 2013/0252318 A1 Sep. 26, 2013

Related U.S. Application Data

(62) Division of application No. 13/374,195, filed on Dec. 14, 2011, now Pat. No. 8,497,119.

(51) Int. Cl.
| | | |
|---|---|---|
| *A01B 1/00* | (2006.01) | |
| *C12M 3/00* | (2006.01) | |
| *C12N 5/075* | (2010.01) | |
| *C12M 1/42* | (2006.01) | |

(52) U.S. Cl.
CPC ........... *C12N 5/0609* (2013.01); *C12M 21/06* (2013.01); *C12M 35/00* (2013.01)

(58) Field of Classification Search
CPC ....... B01L 2400/0415; B01L 3/502761; B01L 2200/0668; B01L 2300/0819; C12M 35/00; C12M 35/04
See application file for complete search history.

(56) References Cited

U.S. PATENT DOCUMENTS

| | | |
|---|---|---|
| 4,619,899 A | 10/1986 | Nikitin et al. |
| 5,114,854 A | 5/1992 | Bertholdt |
| 5,877,008 A | 3/1999 | Remenyik et al. |
| 6,592,552 B1 | 7/2003 | Schmidt |
| 7,855,067 B2 | 12/2010 | Sasaki et al. |
| 2002/0076689 A1* | 6/2002 | Farb et al. .......... 435/4 |
| 2002/0098575 A1* | 7/2002 | Mathes et al. ........ 435/287.3 |
| 2006/0154233 A1* | 7/2006 | Deutsch .............. 435/4 |
| 2013/0065795 A1* | 3/2013 | Allbritton et al. ........ 506/26 |

* cited by examiner

*Primary Examiner* — Nathan Bowers

(57) ABSTRACT

A device for performing micro-operations on a vesicular target, comprising an injection pipette (27); a barrel assembly (9); and an outer assembly (1). The injection pipette, barrel assembly, and outer assembly being designed and situated in relation to each other such that an axial vacuum passage is created between the injection pipette and the barrel assembly, and a radial vacuum passage is created between the barrel assembly and outer assembly, and such vacuum passages are isolated from each other and from atmospheric pressure (FIG. 8). The device also comprises a means of advancing and withdrawing the distal end of the barrel assembly in relation to the distal end of the outer assembly so as to create a holding well (31) and a means of advancing the pipette into, and withdrawing the pipette from, a vesicular object.

1 Claim, 8 Drawing Sheets

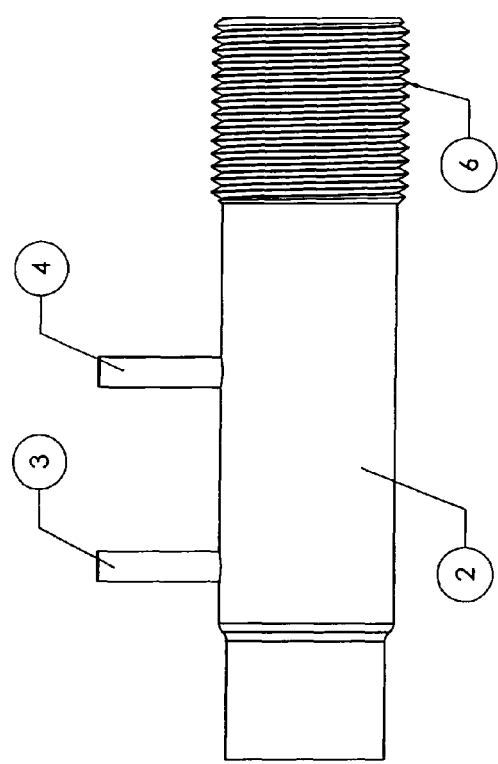
FIG. 5
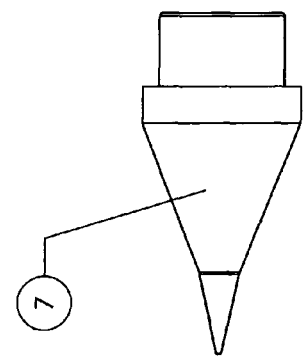
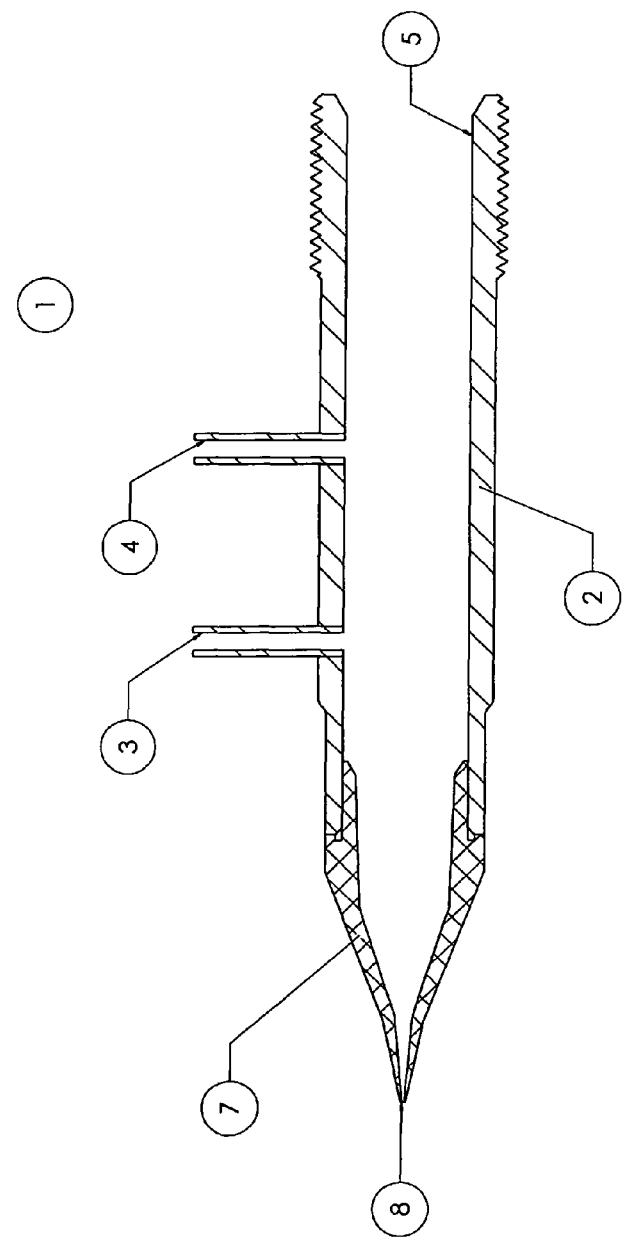
FIG. 6

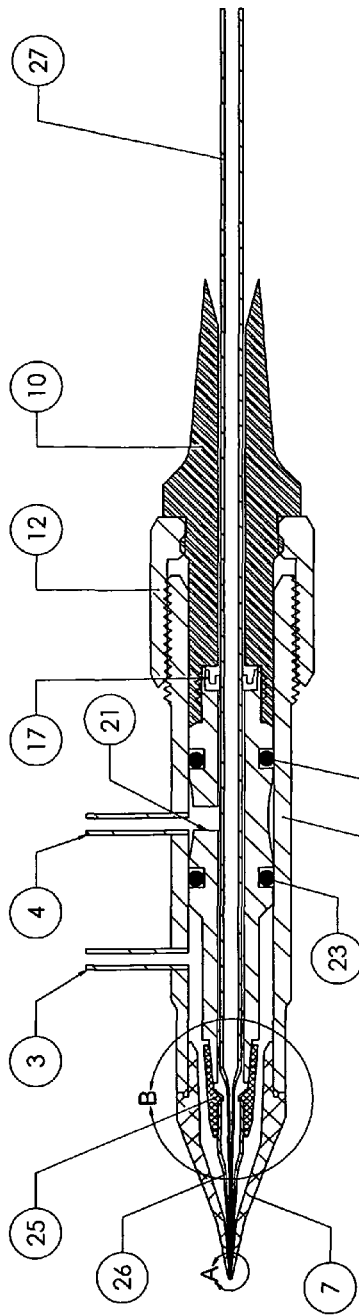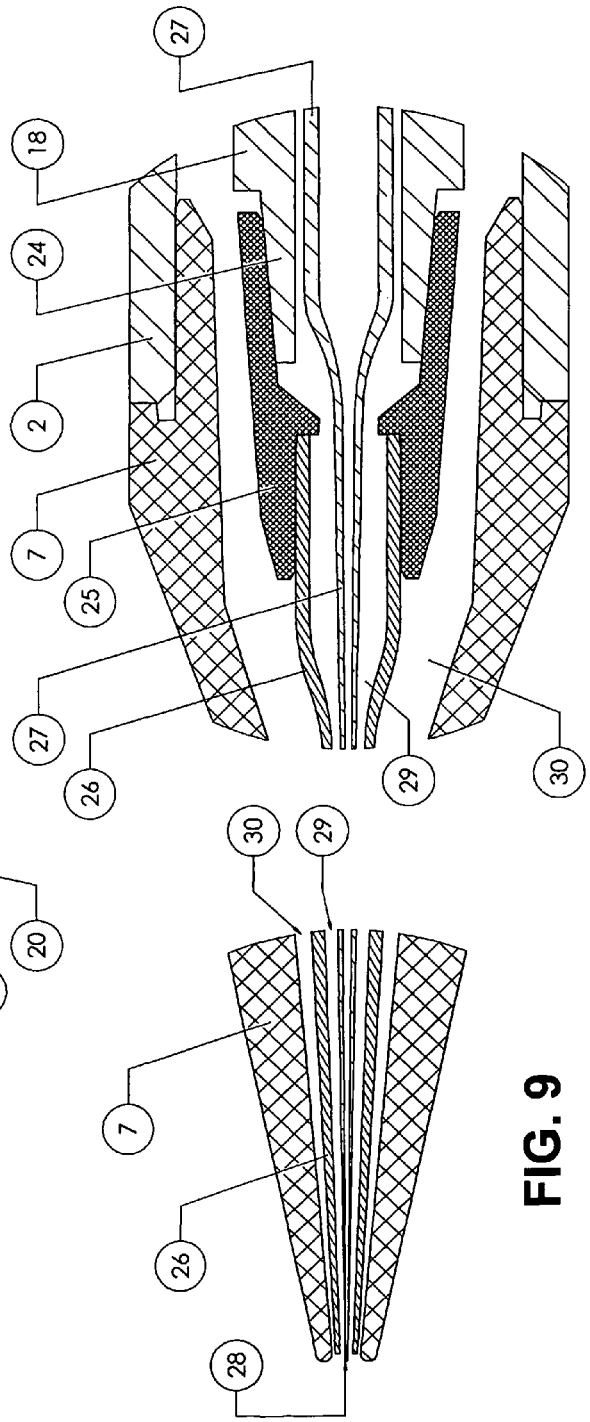

DEVICE FOR PERFORMING MICRO-OPERATIONS ON A VESICULAR OBJECT

CROSS-REFERENCE TO RELATED APPLICATIONS

1. This application is a division of application Ser. No. 13/374,195 filed Dec. 14, 20144, now U.S. Pat. No. 8,497, 119, granted Jul. 30, 2013.
2. This application also claims the benefit of PPA Ser. No. is 61/459,577 filed Dec. 15, 2011 by the present inventor, which is incorporated by reference.

FEDERALLY SPONSORED RESEARCH

This invention was not made under a government contract and the government has no rights in it.

SEQUENCE LISTING OR PROGRAM

Not applicable.

BACKGROUND

Prior Art

The following is a tabulation of some prior art that presently appears relevant:

U.S. PATENTS

| Pat. No. | ISSUE DATE | PATENTEE |
| --- | --- | --- |
| 4,619,899 | October 1986 | Nitikin, et al. |
| 5,114,854 | May 1992 | Bertholdt |
| 5,877,008 | March 1999 | Remenyik, et al. |
| 6,592,552 B1 | July 2003 | Schmidt |
| 7,855,067 B2 | December 2010 | Sasaki, et al. |

FOREIGN PATENT DOCUMENTS

Foreign Doc. Nr.

10-2005-0023483
WO 2009/070474 A1

NON-PATENT LITERATURE DOCUMENTS http://www.eppendorf.com/int/img/na/lit/pdf8301-C110G-07.pdf

BACKGROUND

The present application relates to a device for holding, puncturing and manipulating the contents of a vesicular object having a size typically in the neighborhood of 100-300 microns. This device has particular application for manipulation of mammalian embryos at the hatched blastocyst stage of development. This has not been possible with any previous device.

Working with the hatched blastocyst has been difficult because the blastocysts are spherical vesicular structures consisting of a thin envelope of living cells surrounding a relatively large central cavity that is filled with an aqueous fluid. The difficulty, and the failure of the prior art, arises because of the physical characteristics of the envelope of these living cells which may be flimsy but resistant to puncture. For example, holding a hatched blastocyst by vacuum from one side with a conventional glass holding pipette while attempting to puncture it by compression from the opposite side with a conventional glass injection pipette often simply indents the blastocyst surface without puncturing it, or conversely, ends up destroying the integrity of the envelope of living cells altogether. This compression can be severe and potentially damaging to the living cells. With the present device there is no compression at all. A portion of the nearside of the surface of the embryo can be grasped and stretched tight for easy penetration.

Additionally, conventional methods disclosed by the prior art require expensive micromanipulators for positioning of the two pipettes required (one for holding and one for injection) in 3-axes so they are perfectly aligned for puncture of the vesicular object by compression. Because the forces compressing the spherical embryo have to be exactly aligned for penetration, both the holding and injection pipettes, presented from above, must have a 30 degree bend near the tip so they can be parallel to the floor of the dish and to each other. None of this is necessary with the present device.

ADVANTAGES OF THE EMBODIMENT

The present device overcomes the above-described difficulties by providing a device which, using vacuum, firmly holds a portion of the surface of the blastocyst prior to piercing. This allows "volume reduction", aspiration, of the contained non-essential aqueous fluid, called blastocoel fluid. This process of water-volume reduction, allows for freezing protocols that involve less exposure to toxic Cryoprotectant solutions. With the present device, this fluid may be aspirated through the lumen of a standard glass injection pipette or, in a process unique to this device and due to the device's unique double vacuum passages, contained fluid can be aspirated rapidly around the injection pipette through the aperture at the distal end of the inner tip.

This capability for rapid extraction of fluid around the injection pipette provides the additional benefit of allowing simultaneous injection into and aspiration from an object's total fluid volume. This allows the total contained volume to be held constant, even during replacement of the blastocoel fluid with a cryoprotectant solution before freezing, thus preventing physical damage to the early embryos of some species that cannot tolerate complete embryonic collapse. As used herein, use of the word "fluid" includes any solids, including for example, DNA or other genetic material, associated with that fluid.

These and other advantages of one or more aspects of the device will become apparent from a consideration of the ensuing description and accompanying drawings.

SUMMARY, CONCLUSION, RAMIFICATIONS, AND SCOPE

The above-described device, using vacuum applied between the two concentric tips, firmly holds a portion of the surface of any small vesicular object, including any pre-implantation embryo of any species of mammal, for puncture. Due to the present device's unique double vacuum passages, fluid can be injected into the vesicular object while fluid is simultaneously extracted from that vesicular object. The device allows for the above-described procedures to be done with the widely available stereoscope thereby expanding the number of facilities capable of performing many procedures.

The device can have a dedicated micromanipulation module attached at its distal end for precise control of the injection pipette, which passed down through the axial space of the device. Future versions of the basic device may have micromanipulation capabilities for movement of the injection pipette integrated into the device itself. This embodiment will be for use on smaller, earlier-stage embryos and will usually be used with inverted microscopes. It can include the capability for rapid forward and back oscillation of the pipette by a few microns, resulting in a piezo hammer or impact drill effect, for easy penetration of hard objects like the zona pellucida of the oocyte and early blastocyst.

BRIEF DESCRIPTION OF THE DRAWINGS

FIG. 5 is an elevational view of the vacuum jacket and outer tip;

FIG. 6 is a cross-sectional view of the assembled vacuum jacket and outer tip shown in FIG. 5;

FIG. 8 is a cross-section of the device shown in FIG. 1;

FIG. 9 is a detail view at "A" shown in FIG. 8;

FIG. 10 is a detail view at "B" shown in FIG. 8;

REFERENCE NUMERALS

1. Outer Assembly
2. Vacuum Jacket
3. Radial Vacuum Port
4. Axial Vacuum Port
5. Inside of Vacuum Jacket
6. Threads on Outer Surface of Vacuum Jacket
7. Outer Tip
8. Primary Aperture
9. Barrel Assembly
10. Upper Barrel
11. External Threads on Upper Barrel
12. Coupling
13. Knurled Outer Surface of Coupling
14. Internal Distal Threads on Inner Surface of Coupling
15. Internal Threads in Upper Barrel
16. External Threads on Lower Barrel
17. Inner Seal
18. Lower Barrel
19. Groove for Proximal O-ring
20. Proximal O-ring
21. Shunt
22. Groove for Distal O-ring
23. Distal O-ring
24. Nipple of Lower Barrel
25. Ferrule
26. Inner Tip
27. Injection Pipette
28. Open Tip of Pipette
29. Axial Vacuum Passage
30. Radial Vacuum Passage
31. Holding Well
32. Secondary Aperture
33. Central Bore
34. Vesicular Object, Especially the Envelope of Living Cells of an Early Embryo
35. Internal Proximal Threads on Inner Surface of Coupling

DETAILED DESCRIPTION OF AN EMBODIMENT

Elements

Figure 1:
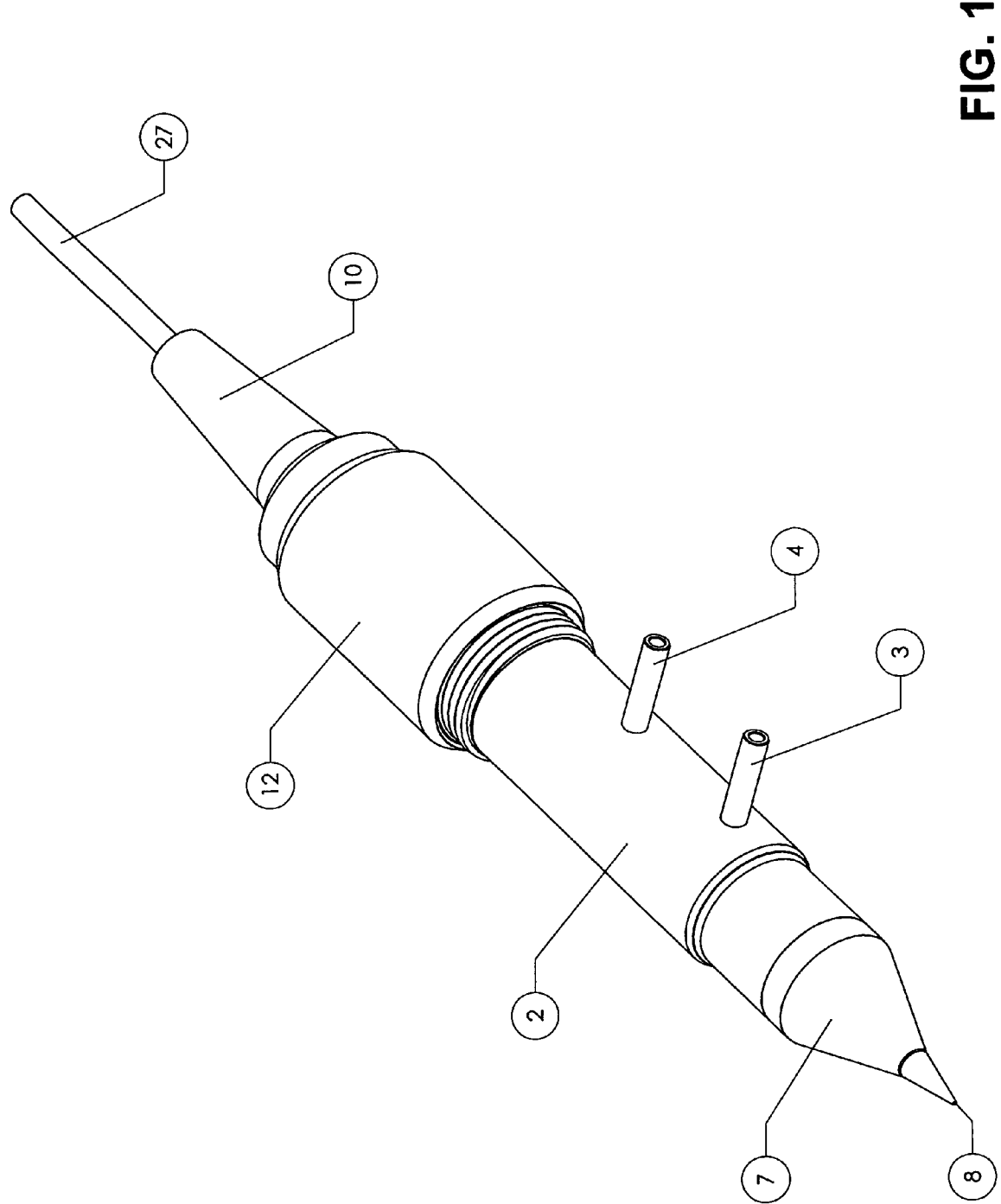
FIG. 1 is a perspective view of the device.
Figure 7:
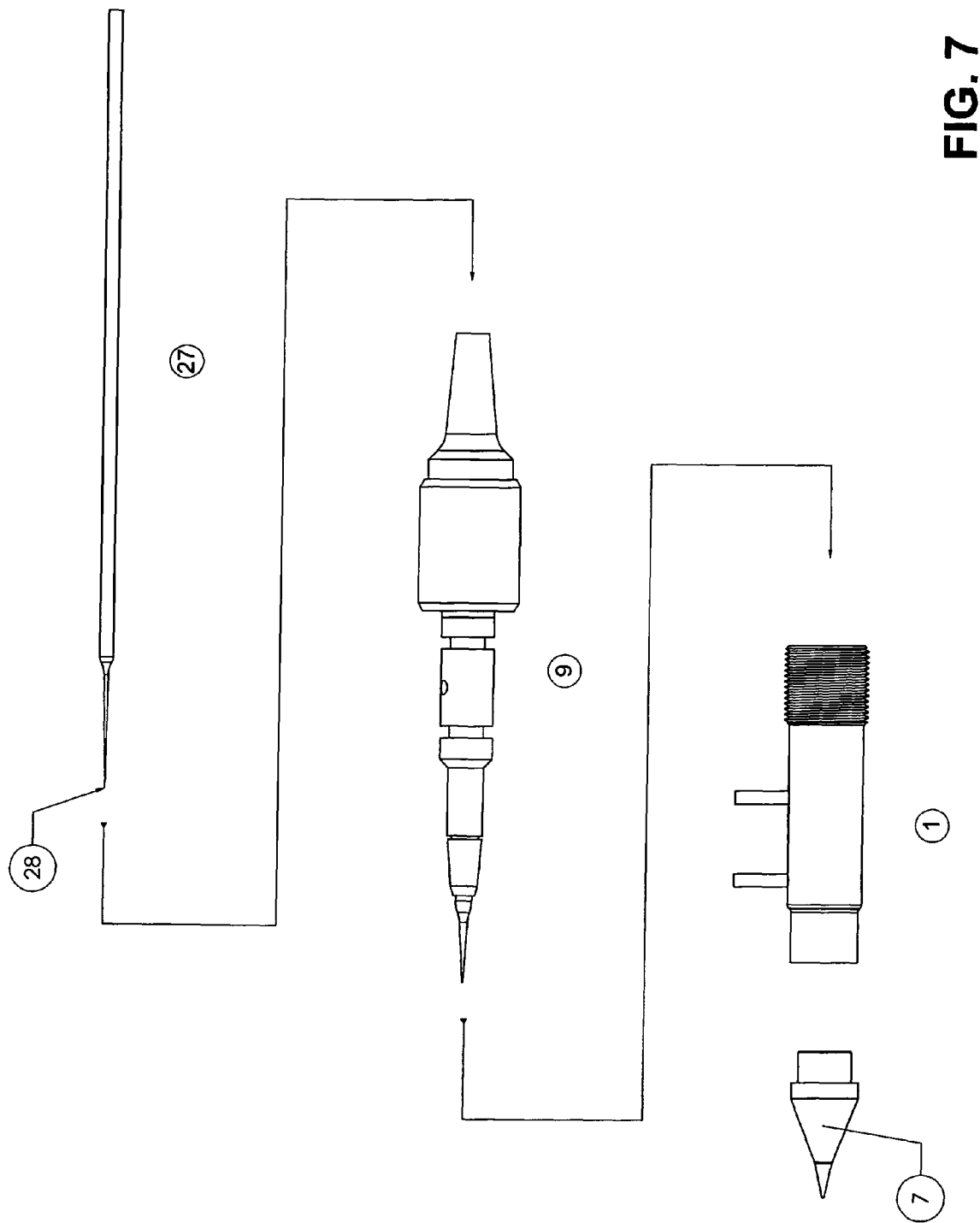
FIG. 7 is an assembly diagram of the components of the device shown in FIG. 1.

A device for performing micro-operations on a vesicular object is shown in FIG. 1. In this embodiment, in addition to a pipette (27) capable of injection and aspiration through an opening in its distal end (28), the device includes two separate generally cylindrical assemblies. The first assembly is an outer assembly (1) and the second assembly is a barrel assembly (9). The barrel assembly (9) is inserted into the outer assembly (1) as shown in FIG. 7.

Outer Assembly

Figure 3:
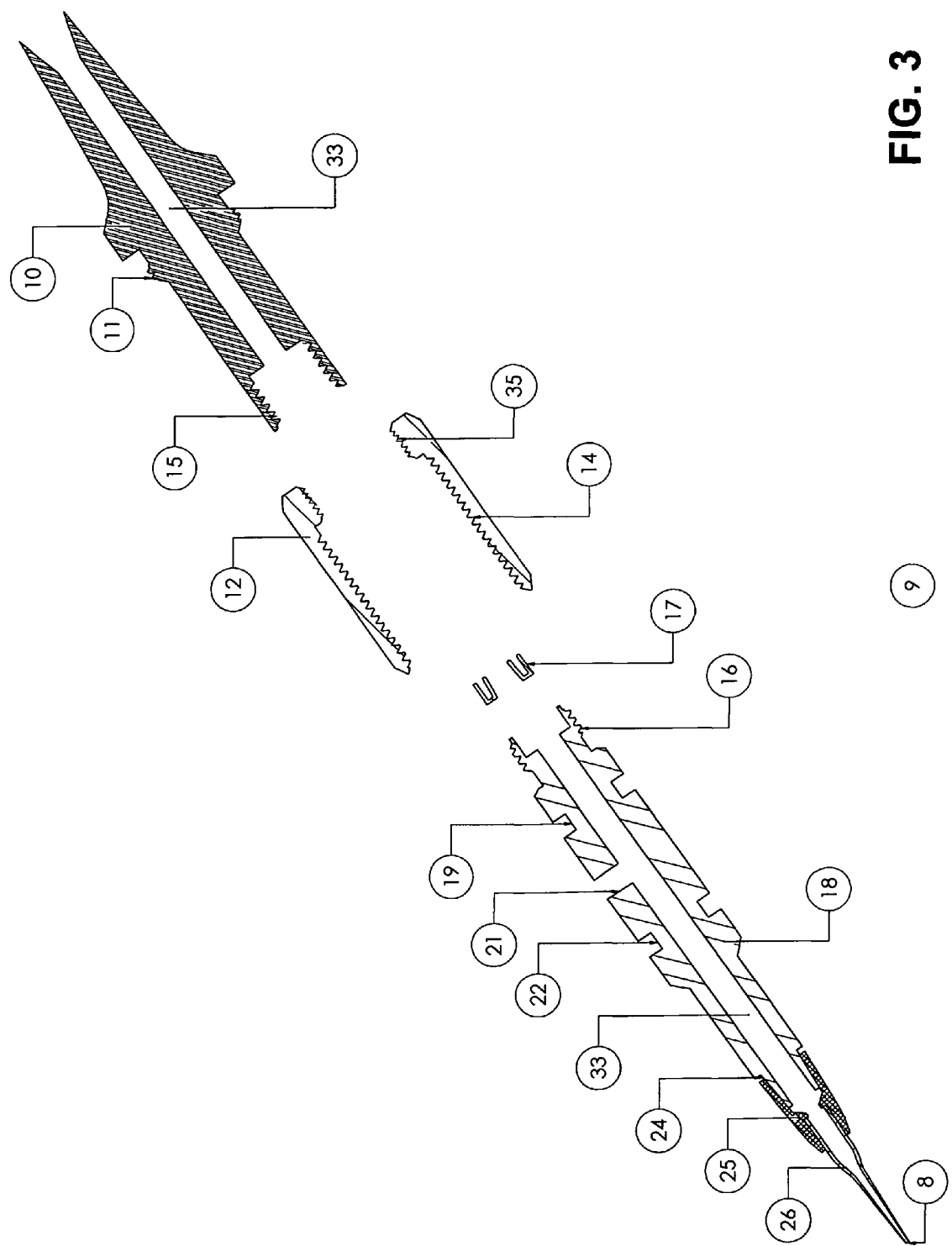
FIG. 3 is an exploded cross-section view of a barrel assembly used with the present device.

The outer assembly comprises a vacuum jacket and an outer tip. FIG. 5. The vacuum jacket (2) includes a main body portion open at both ends. A conical outer tip, FIG. 5 (7) is frictionally fitted at one end of the vacuum jacket (2) as shown in FIG. 6. The inside diameter of the outer tip at its distal end (7) defines an opening, the primary aperture (8). FIGS. 1 and 3.

Figure 2:
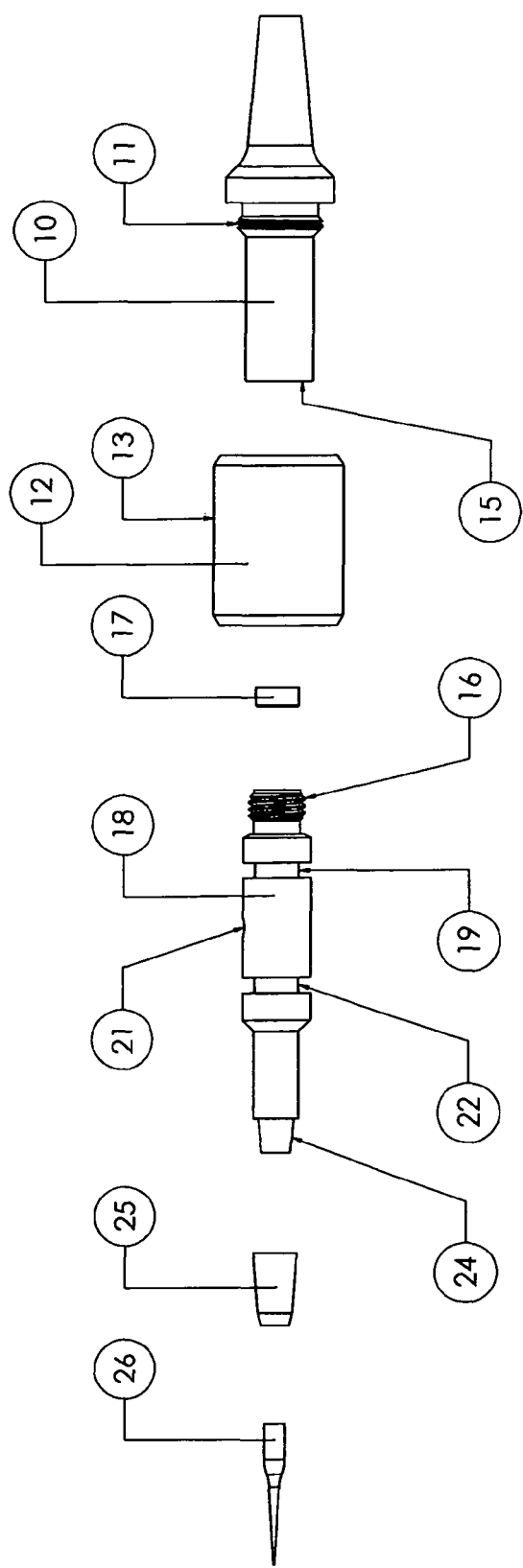
FIG. 2 is an elevational exploded view of the components of the barrel assembly used with the present device.

The vacuum jacket (2) is provided with external threads FIG. 5 (11) at its proximal end, for threadably engaging internal threads FIG. 3 (14) provided inside a rotatable coupling FIG. 2 (12) such coupling being attached to the upper barrel FIG. 2 (10) by means of external threads (11) on the upper barrel (10). The knurled outer surface (13) of the coupling (12) allows the user to easily thread the barrel assembly (9) into the vacuum jacket FIG. 7. The vacuum jacket is also provided with a radial vacuum port FIG. 6 (3) and an axial vacuum port (4) both of which extend through the wall of the vacuum jacket (2). These vacuum ports provide fluid communication to the interior of the vacuum jacket.

Barrel Assembly

Figure 4:
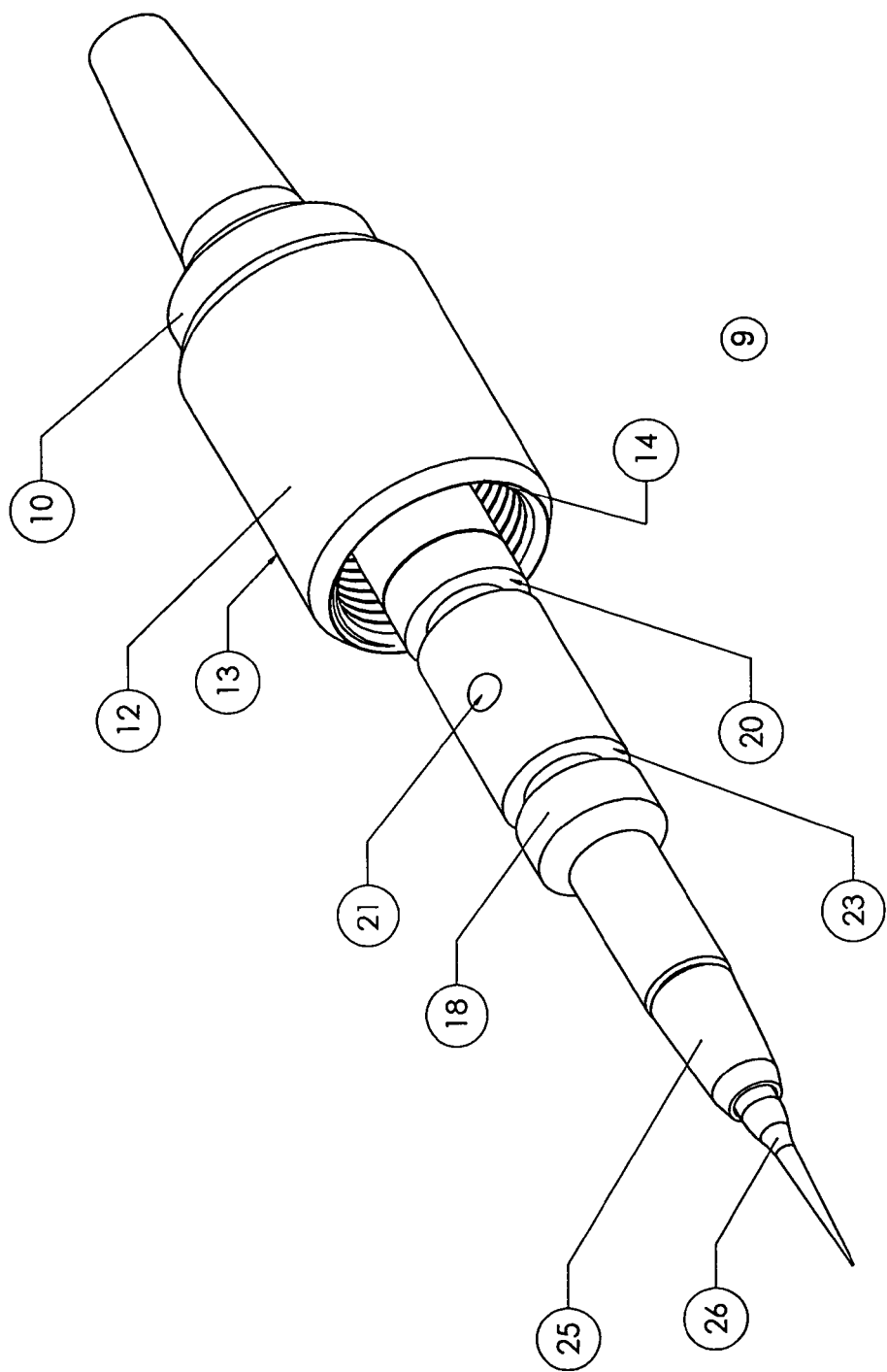
FIG. 4 is a perspective view of the barrel assembly used with the present device.

In this embodiment—the barrel assembly FIG. 4 (9) includes an upper barrel (10), a lower barrel (18), a rotatable coupling (12), a spring-energized inner seal positioned between the upper and lower barrel FIG. 3 (17), a ferrule (25) for frictional attachment of the lower barrel to the proximal end of the inner tip, and an inner tip (26). The upper barrel (10) is provided with a blind bore for threadably receiving the lower barrel (18) as shown in FIG. 3.

The lower barrel (18) has external threads (16) for mating with internal threads (15) located within the blind bore provided at the distal end of the upper barrel (10) as shown in FIG. 8. The proximal end of the lower barrel has, inside its threaded end, a blind bore for seating of the inner seal (17). Both the lower barrel (18) and the Upper barrel (10) are provided with co-aligned axial bores forming a continuous central bore. FIG. 3. (33).

The coupling FIG. 3 (12) has distal internal threads (14) for mating with the external threads (6) on the outer surface of the vacuum jacket (2) and proximal internal threads (35) for mating with the external threads (11) on the upper barrel (10). Although it is possible for the coupling and the upper barrel to be manufactured in one piece.

Figure 11:
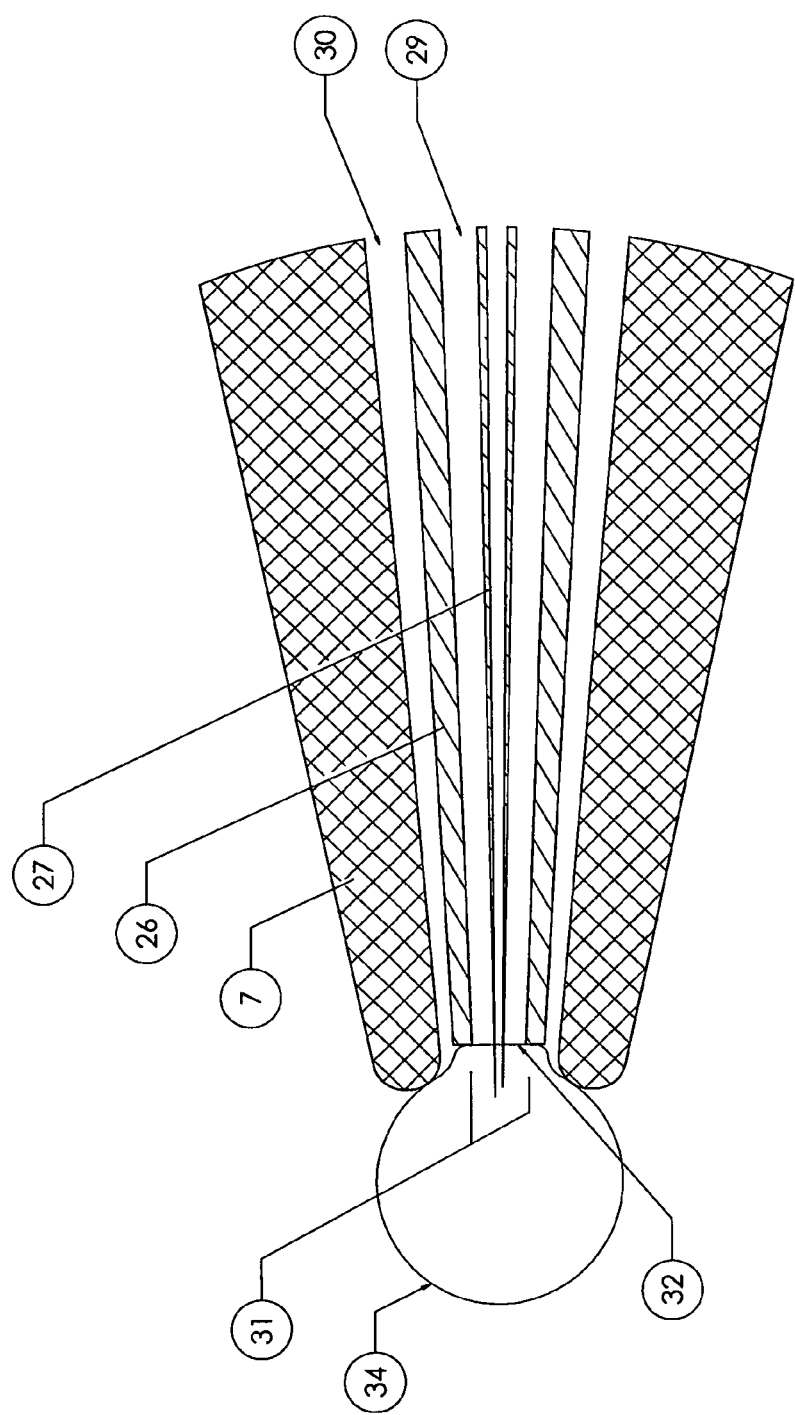
FIG. 11 is a detail cross-sectional view of the distal end of the device (the tip) shown in use, with the pipette advanced and having pierced a vesicular object.

An injection pipette FIG. 7 (27) is slidably received by the axial bores. The axial bores are sized to leave an axial vacuum passage FIG. 10 (29) between the outer surface of the injection pipette (27) and the inside of the axial bore in the lower barrel (18). FIG. 10. Such axial vacuum passage extending along the outside of the injection pipette and terminating at the aperture of the inner tip (secondary aperture) shown in FIG. 11. (32). The injection pipette (27) includes a tapered needle end and opening (28) at its distal end. FIG. 9. A spring-energized lip seal, the inner seal (17), is used to seal the lower barrel (18) against the injection pipette (27). FIG. 8. The distal end of the lower barrel (18) is further provided with a cylindrical portion having a reduced outside diameter as shown in FIGS. 2 and 3. The outside diameter of the cylindrical portion is less than the inside diameter of the outer tip (7) as shown in FIG. 10 to provide a radial vacuum passage (30) terminating between the inside of the outer tip (7) and outside of the inner tip (26) as shown in FIGS. 10 and 11. This provides a circular ring of potential holding force to grasp a portion of the surface of the vesicular object by vacuum. In this embodiment, the distal end of the lower barrel (18) is a metal nipple (24) designed to fit, via self-locking taper, into a stopped bore at the proximal end of a plastic ferrule FIG. 2 (25). The proximal end of the inner tip (26) is frictionally fitted into a stopped bore at the distal end of the ferrule (25) as detailed in FIGS. 2 and 3. The inner tip (26) open at both ends, functions as a guide when the needle end (28) of the injection pipette is extended through the secondary aperture at the distal end of the inner tip FIG. 11 (32). The distal end of the inner tip also provides a floor for the holding well FIG. 11 (31).

The ferrule FIG. 2 (25) provides a positive seal between the lower barrel nipple FIG. 2 (24) and the inner tip (26) while also providing a flexible joint to insure the inner tip (26) can align concentrically within the primary aperture (8) of the outer tip FIG. 8 (7) during use. The lower barrel (18) is also provided with grooves (19) and (22) as shown in FIG. 2 for receiving O-rings (20) and (23) as shown in FIG. 8.

The lower barrel (18) is also provided with a shunt, that is, a hole passing from the outer surface of the lower barrel into the central bore. FIG. 8 (21) that places the axial vacuum port (4) in fluid communication with the portion of the axial vacuum passage (29) surrounding the pipette (27). FIG. 10.

Interrelationship of Elements

As shown in FIGS. 8 through 10, when a vacuum is applied through the radial vacuum port (3) the vacuum is in fluid communication with the radial vacuum passage (30). When a vacuum is applied to the axial vacuum port (4), the vacuum is in fluid communication, by means of the shunt (21), with the axial vacuum passage (29), such passage extending from the shunt, distally along the pipette, and terminating at the aperture of the inner tip, the secondary aperture FIG. 11. (32).

As shown in FIG. 9), the position of distal end of the inner tip (26) in relation to the distal end of the outer tip (7), is adjusted with the threaded coupling (12) connecting the vacuum jacket (2) and the barrel assembly (9). FIG. 8.

This provides, and determines the shape of, a holding well FIG. 11 (31), formed by the combination of inner and outer tips at the distal end of the device, for holding a vesicular object such as an embryo or other vesicular structure. FIG. 11.

Operation

1. As shown in FIG. 7, in operation of the present embodiment, the barrel assembly (9) is inserted through the opening in the proximal end of the outer assembly (1) and, by rotation, the threaded coupling (12) on the barrel assembly is used to advance or withdraw the distal end of the inner tip (26) in relation to the distal end of the outer tip (7) to form the desired contour of the holding well (31) as shown in FIG. 11.

2. An injection pipette (27) is slidably inserted through the bores provided in the barrel assembly (9), passing through the inner seal (17). The position of the injection pipette (27) is slidably adjusted so that the needle end (28) of the injection pipette (27) is slightly retracted from the inner tip opening, the secondary aperture (32). FIG. 11. A vesicular object such as a blastocyst, as shown in FIG. 11, is positioned immediately in front of the primary aperture FIG. 6 (8) of the outer tip (7).

3. A vacuum source (not shown) is connected to the radial vacuum port (3) and a second vacuum source (not shown) is connected to the axial vacuum port (4). FIG. 8. With vacuum applied to the radial vacuum port (3), vacuum through the radial vacuum passage (30) securely holds the vesicular object to the circular ring between inner and outer tips, within the holding well FIG. 11 (31) formed just inside the primary aperture (8).

4. The final position of the inner tip (26) may then be advanced or withdrawn as needed to produce the desired relation with the surface of the vesicular object using the threaded coupling (12) so that the inner tip rests against, and seals against, the secured object. FIG. 11. At which point the vacuum in passage (30) acts only on the ring of the vesicular object's surface in the area (30) between the distal end of the inner tip (26) and the distal end of the outer tip (7). FIG. 11.

5. Vacuum can be applied to the axial vacuum port (4) and thereby to axial vacuum passage (29), to draw the exact point of penetration of the vesicular object surface tightly against the secondary aperture (32) in the distal end of the inner tip at the moment of penetration. FIG. 12.

6. The needle end (28) of the injection pipette (27) may then be slidably extended to pierce the outer surface of the vesicular object. FIG. 11.

7. Fluid can then be injected into, or aspirated from, the vesicular object through the lumen of the injection pipette (27).

8. Vacuum can be applied to the axial vacuum port FIG. 8 (4) and thereby to axial vacuum passage (29), to draw fluid from the central volume of the object through the secondary aperture (32), that is, from between the inside of the inner tip (26) and the outside of the open tip of the pipette (28). FIG. 11.

9. With this procedure, it is possible to inject into or withdraw fluid from the central volume of the vesicular object via the injection pipette (see Step 7 above) and also to aspirate from the central volume of the vesicular object via the secondary aperture (see Step 8 above) simultaneously.

10. Another effect of the vacuum applied to the axial vacuum port (4) is to draw the external surface of the vesicular object taut across the secondary aperture (32), and allow for easy puncture with the needle end (28) of the pipette (27) as shown in FIG. 11.

This apparatus has particular advantage when working with a hatched blastocyst where the external surface of the embryo is very flimsy so it cannot be held on one side and punctured from the opposite side by compression.

While the above description contains many specificities, these should not be construed as limitations on the scope of any embodiment, but as examples of various embodiments thereof. Many other ramifications and variations are possible within the teachings of the various embodiments without departing from the scope of the device disclosed above. Thus the scope should be determined by the appended claims and their legal equivalents, and not by the examples given.

I claim:

1. A device for performing micro-operations on a vesicular target, comprising:

a, an injection pipette capable of injection or aspiration (27) such pipette having an opening at its distal end (28);

b, a barrel assembly (9) having an inside diameter larger than the outside diameter of the pipette so as to create an axial vacuum passage (29) between the outside of the pipette (27) and the inside of the barrel assembly (9), such axial vacuum passage terminating at a secondary aperture (32), the barrel assembly is provided with external O-rings (20 and 23) situated on either side of a shunt (21) through the barrel assembly wall, the distal end of the barrel assembly forming an inner tip (26);

c, an outer assembly having an inside diameter larger than the outside diameter of the barrel assembly so as to create a radial vacuum passage between the inside of the outer assembly and the outside of the barrel assembly (30), such radial vacuum passage terminating at its distal end at a primary aperture (8), the outer assembly having both a radial vacuum port (3) and an axial vacuum port (4), the distal end of the outer assembly forming an outer tip (7);

d, the barrel assembly (9) being inserted into the outer assembly (1) and the injection pipette (27) being inserted into the barrel assembly;

e, the injection pipette, barrel assembly, and outer assembly being designed and situated in relation to each other such that the axial vacuum passage between the pipette and the barrel assembly, via the barrel assembly shunt (21), is in fluid contact with the axial vacuum port, and the radial vacuum passage between the barrel assembly and outer assembly, is in fluid communication with the radial vacuum port, and, due to the external O-rings (20 and 23) between the barrel assembly and the outer assembly, the axial and radial passages are isolated from each other and from atmospheric pressure;

f, a coupling (12) securely attached to an upper barrel assembly (10);

g, external threads (6) on the proximal end of the outer assembly (11);

h, said coupling (12) having interior threads (14) and being of such size and designed so as to receive and engage the exterior threads (6) on the outer assembly (1), the rotation of such barrel assembly either advancing or withdrawing the inner tip in relation to the outer tip so as to create a holding well (31) to cradle the surface of the embryo or other vesicular object;

whereby allowing: the position of the distal end of the barrel assembly, that is, the tip of the inner tip (26), to be adjusted in relationship to the distal end of the outer assembly, that is, the tip of the outer tip (7), by rotating the barrel assembly, via the coupling, thereby creating the desired contour of the holding well (31), and allowing the simultaneous holding of the vesicular object at the primary aperture by applying negative pressure in the radial vacuum passage; injection into or aspiration from the vesicular object via the pipette; and aspiration from the vesicular object at the secondary aperture (32) by applying negative pressure in the axial vacuum passage.

* * * * *